United States Patent [19]

Smith

[11] Patent Number: 4,965,900
[45] Date of Patent: Oct. 30, 1990

[54] ABSORBENT DEVICE

[76] Inventor: Gary D. Smith, 1901 Highway, 41 North, Rm. #43, Evansville, Ind. 47711

[21] Appl. No.: 426,241

[22] Filed: Oct. 25, 1989

[51] Int. Cl.$^5$ .............................................. A61G 9/00
[52] U.S. Cl. ........................................... 5/463; 5/484
[58] Field of Search ............... 4/451, 456; 5/463, 470, 5/484, 987, 501

[56] References Cited

U.S. PATENT DOCUMENTS

| | | | |
|---|---|---|---|
| 2,614,273 | 10/1952 | Yanoufski | 5/484 X |
| 2,741,781 | 9/1956 | Rudisell | 5/484 |
| 3,691,570 | 9/1972 | Gaines et al. | 5/487 |
| 3,757,356 | 9/1973 | Freeman | 5/463 |
| 3,812,001 | 5/1974 | Ryan | 5/484 X |
| 3,889,302 | 6/1975 | Ketterer et al. | 5/484 X |
| 4,173,046 | 11/1979 | Gallagher | 5/484 |
| 4,752,293 | 6/1988 | Smith | 5/463 X |

Primary Examiner—Michael F. Trettel
Attorney, Agent, or Firm—Donald J. Breh

[57] ABSTRACT

An absorption pad for a bed is disclosed including a bag like member having an upper and a lower compartment, a moisture impervious periphery and bottom and a moisture permeable top covering and internal divider wall. A non-absorbant, moisture permeable cushion is encased in the upper compartment and a removable filter member including a non-absorbant moisture permeable filter cushion member having an internal moisture absorbing element and support members is disposed in the lower compartment.

19 Claims, 2 Drawing Sheets

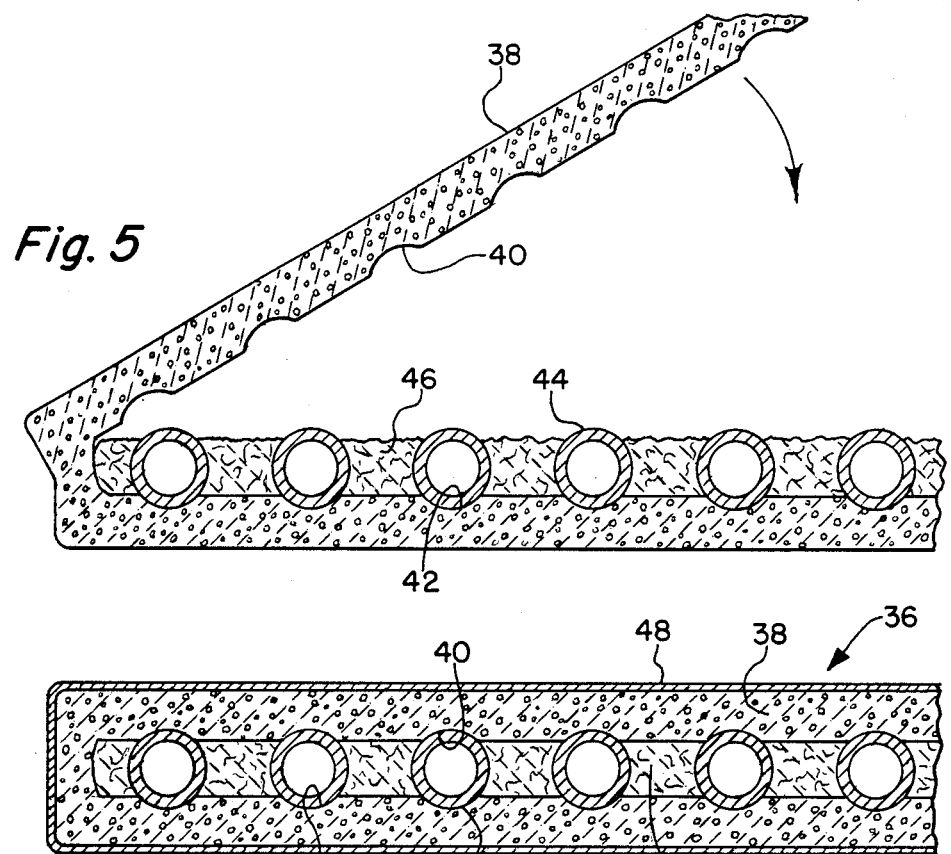
Fig. 5
Fig. 6
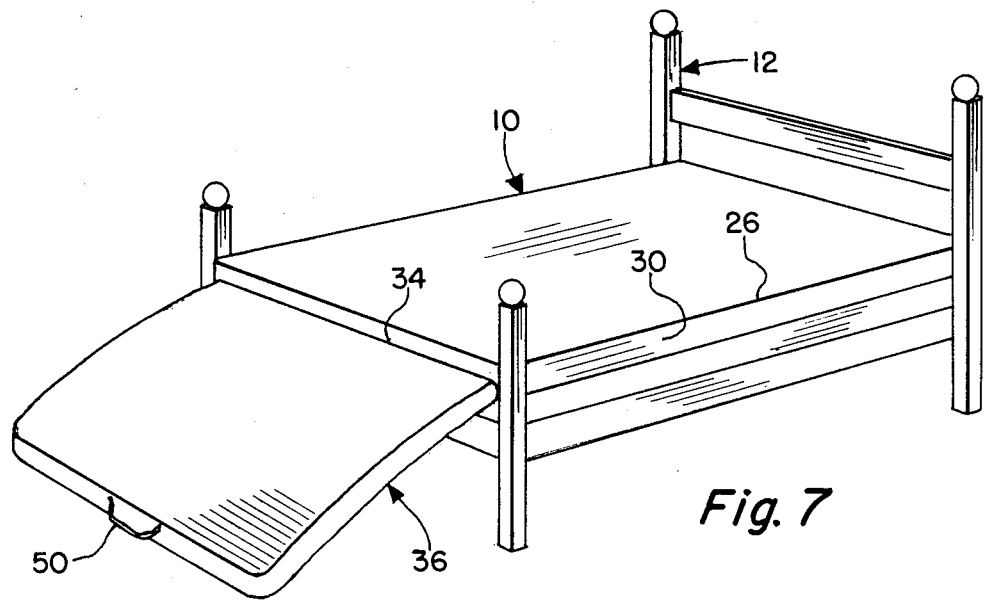
Fig. 7

ABSORBENT DEVICE

BACKGROUND OF THE INVENTION

This invention relates to an absorbent device for use with beds and in particular to an absorbent device which has improved effectiveness in protecting bedding on which the device is placed and in maintaining a dryer area which will be occupied by a user's body than prior art devices.

Absorbent pads and devices for bedding to collect body fluids and excretions such as urine exist and include, among others, simple moisture impervious liners or pads which can be effective in protecting bedding by acting as a physical barrier to the passage of fluids but which are not effective in maintaining the area occupied by a user dry.

Other devices utilizing absorbent pads of one design or another, while more effective in maintaining the area to be occupied by the user dry, are typically not easily cleaned, have short life and still further improvement in pad useful life and collection, removal and storage of such fluids is desirable.

SUMMARY OF THE INVENTION

Accordingly, the present invention provides for an absorbent pad particularly adapted for use on a bed which has improved life and fluid collection, removal and retention characteristics.

According to a preferred embodiment of the invention, there is provided a bag like container having two internal compartments, one housing a cushion which is adapted to allow passage of moisture into a lower compartment wherein there is housed a filter cushion member which absorbs and retains fluids.

According to an important feature of the invention, the top cushion is a non-absorbent, moisture permeable cushion encased in a non-absorbent moisture permeable casing.

According to another feature of the invention, there is provided a moisture impervious casing attached to the top perimeter of the top cushion to form a water tight lower compartment.

According to a still further important feature of the invention, the filter cushion member includes a non-absorbent, moisture permeable, semi-supportive, resilient member having an internal absorbent element.

According to a still further important feature of the invention, the filter cushion member includes a plurality of spaced apart transverse support members embedded within the non-absorbent permeable, semi-supportive, resilient member.

According to another important feature of the invention, the filter cushion member includes an absorbent element within the non-absorbent, moisture permeable, semi-supportive, resilient member.

According to yet another feature of the invention, the filter cushion member is encased in a non-absorbent, moisture permeable casing.

Another very important feature of the invention provides for an access opening into the lower compartment of the absorbent device and the filter cushion member is removable from the lower compartment for cleaning.

BRIEF DESCRIPTION OF THE DRAWINGS

The invention will be better understood after a reading of the following Detailed Description of the Preferred Embodiment in conjunction with the drawings in which:

FIG. 5 is a partial cross sectional view of the filter cushion member showing details of construction;

FIG. 6 is a partial cross sectional view of the filter cushion member showing further details of construction and assembly; and FIG. 7 is a pictorial view of a typical bed and absorbent device according to the invention showing the filter cushion member being removed or inserted from the device.

DETAILED DESCRIPTION OF THE PREFERRED EMBODIMENT

Figure 2:
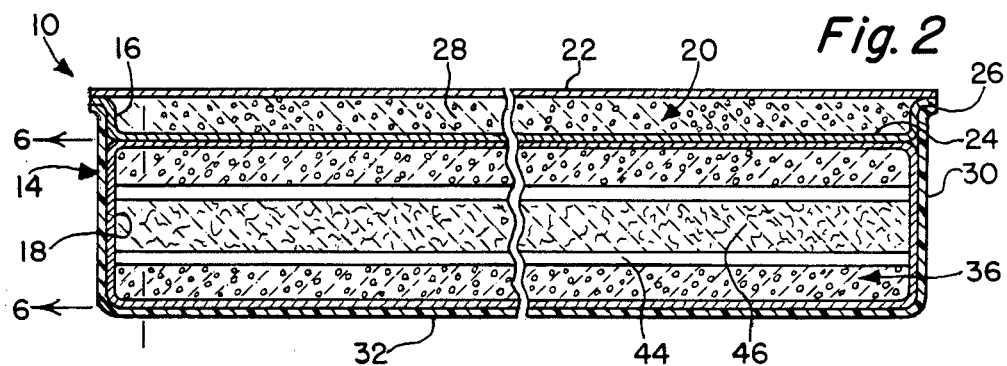
FIG. 2 is a vertical transverse cross sectional view taken along the line 2—2 in FIG. 1 showing details of construction.
Figure 3:
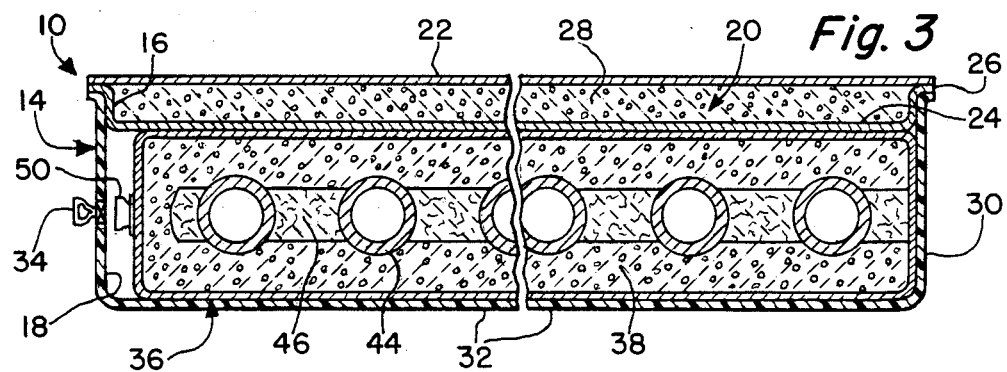
FIG. 3 is a vertical longitudinal cross sectional view taken along the line 3—3 in FIG. 1 showing further details of construction.

Shown in FIG. 7 is an absorbent device 10 according to the invention placed on the mattress of a bed 12 to protect the bedding from damage due to for example urine. Referring principally to FIG. 2 and FIG. 3, the absorbent device 10 includes a bag like member 14 subdivided into an upper compartment 16 and a lower compartment 18. The upper compartment 16 is formed by a nonabsorbent, moisture permeable, open weave fabric such as a polyester cloth within which is encased a non-absorbent, open celled, moisture permeable, resilient, supportive upper cushion 28. Sealed to the top peripherial edge 26 of the upper portion of the bag like container is a bag like element made of moisture impervious material such as vinyl having depending peripherial side walls 30 and a bottom wall 32. It can be seen that the lower side covering of the casing which contains the upper cushion 28 forms an internal horizontal wall 24 that subdivides the bag like member 14 into the two (upper and lower) compartments 16 and 18. The peripherial side walls 30 and upper compartment casing walls 22, 24 are all attached together at the peripherial edge 26 to form a water tight connection such as by sewing, a heat seal or adhesive bonding.

Figure 1:
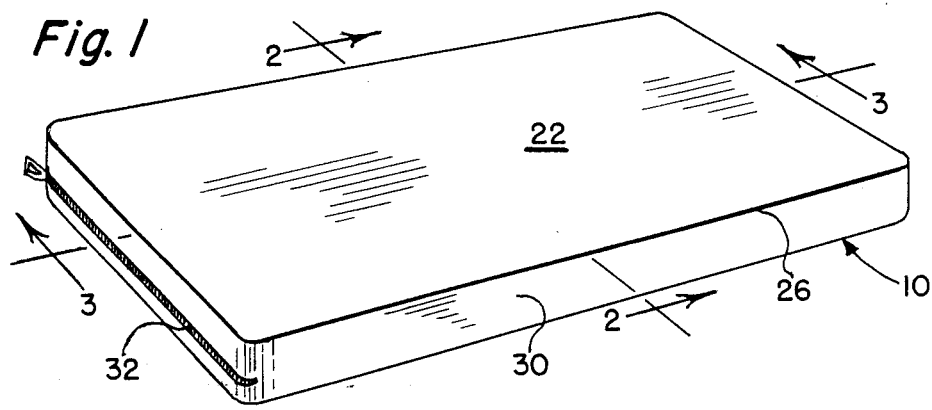
FIG. 1 is a pictorial view of a preferred embodiment of the absorbent device according to the invention.

A self contained filter cushion member 36 is removably housed within the lower compartment 18. As shown in FIGS. 1 and 7, the peripherial wall 30 is provided with a zippered access 32 through which the filter cushion member 36 can be removed from or inserted into compartment 18. The access 32 can be provided either on the end of the device as shown or along a long side of the device if desired to provide access from the side of the bed.

Figure 4:
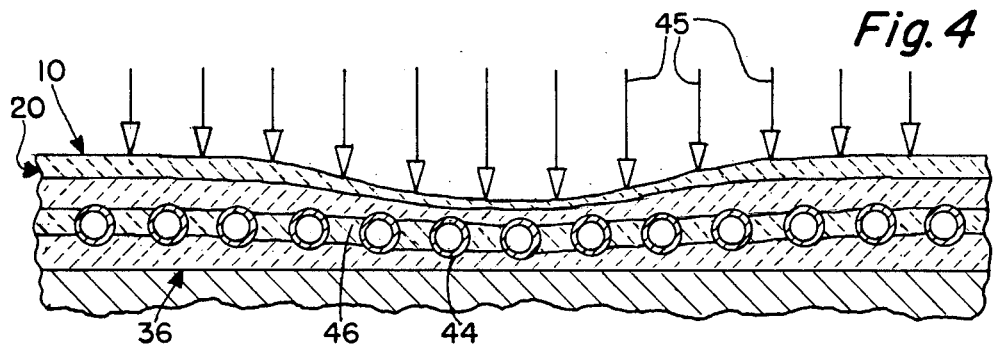
FIG. 4 is a partial cross sectional view of a portion of the absorbent device in use showing details of operation.

As shown in FIG. 3, the filter cushion member 36 occupies substantially the entire volume of the lower compartment 18 and comprises a non-absorbent, moisture permeable, resilient, at least semi-supportive filter cushion element 38 similar to the upper cushion 28 which is encased within a non-absorbent, moisture permeable open weave fabric casing 48 such as a polyester cloth. As shown best in FIGS. 5 and 6, the filter cushion element 38 includes two halves or, as shown in FIG. 5, is of a clam shell type construction wherein the inner surfaces of each half are provided with a plurality of aligned pairs of generally semi-circular, transverse relieved portions such as 40, 42. Positioned within each pair of relieved portions are elongated hard rubber, tubular or cylindrical, longitudinally flexible, but radially non-compressive, support members 44. Positioned between adjacent support members is an absorbent element such as a cotton liner or pads 46. The clam shell or opposing halves of the filter cushion element 38 are closed and glued together against the absorbent element 46 and support tubes 44, as shown in FIG. 6, and the assembly is subsequently encased in the non-absorbent, moisture permeable covering 48. As shown in FIGS. 3 and 7, one end of the filter cushion member 36 is provided with a handle 50 to facilitate insertion and removal of the filter cushion member into and from the compartment 18. If the access 32 is along one long side 30 of the bag like member, the handle would be appropriately placed on a corresponding long side of the filter cushion member. It should be noted that, in use, as shown in FIG. 4, the support rods 44 provide support to the user because, although the support members 44 can flex along their longitudinal axis, because they are non-compressible radially, they limit compression of the filter cushion element 38 to substantially no more than the diameter of the support members 44 and, accordingly, they support the weight of the user's body, as represented by the arrows 45, and, advantageously, the absorbent cotton liner 46 is able to retain moisture since it remains substantially uncompressed under the weight of the user's body.

Further, while the thickness of the filter cushion element 38 is on the order of about 3-4 inches, the upper cushion 28 is substantially thinner and on the order of about ½" thick. The compressibility, and in particular the relative thinness of the upper cushion 28, as well as the compression limiting effect of the support members 44, is important to proper functioning of the device. Referring to FIG. 4, when a user lies on the absorbent device and a liquid or moisture, such as urine, is present, the liquid or moisture passes through the porous outer top covering 22 into the porous upper cushion 28. Although the cushion 28 is non-absorbent and open celled and the vast majority of the moisture passes through the cushion, some moisture is inherently retained within the open cell structure due simply to the size of the cushion. Accordingly, the upper cushion 28 is made relatively thin, but still supportive, whereby the weight of the user, represented by the arrows 45, although still supported, will compress the majority of the thickness of the cushion 28 and force the moisture and liquid out of the upper cushion through lower porous wall 24 into and through the porous casing 48 into the lower filter cushion element 38 of the filter cushion member 36. Eventually, the moisture or liquid passes through the non-absorbent, permeable filter cushion element 38 and enters and is absorbed and retained by the cotton absorbent element 46. As noted, the relatively thin upper cushion 28 is essentially "pumped" by the weight of the user's body to move moisture down into the filter cushion member below for collection and retention. As noted above, the support members prevent the weight of the user's body from compressing the absorbent element 46 and the captured moisture can not be "squeezed" from the absorbent element, but rather remains retained in the element 46. Any moisture that may escape from the absorbent 46, such as when the element becomes saturated with use between cleaning or which naturally escapes by gravity, will be retained within the compartment 18 by the waterproof moisture impervious covering 30, 32. Advantageously, the upper cushion 28, and in particular the top covering 22 that is in contact with the user's body, remains substantially dry. Periodically, the filter cushion member 36 is removed and is easily cleaned by "hosing down" to flush the absorbed liquid from the absorbent element 46 and drying the entire filter cushion member by simple air drying.

Having described the preferrd embodiment of the invention, those skilled in the art having the benefit of that description an the accompanying drawings can readily devise other embodiments and modifications and such other embodiments and modifications are to be considered to be within the scope of the appended claims.

What is claimed is:

1. An absorbent device for a bed or the like comprising:
   a bag like container having a moisture impervious bottom and moisture impervious peripherial sides, a non-absorbent, moisture permeable fabric like top and a non-absorbent moisture permeable divider dividing the container into an upper compartment and a lower compartment;
   a non-absorbent, moisture permeable, resilient cushion in said top compartment; and
   a filter cushion member including a moisture absorbing element removably received in said bottom compartment.

2. The absorbent device as claimed in claim 1 including means for preventing compression of said moisture absorbing element under an external force on said top cushion.

3. The absorbent device as claimed in claim 2 wherein said means for preventing compression includes a plurality of spaced apart support members uniformly and transversely distributed in said filter cushion member.

4. The absorbent device as claimed in claim 3 wherein said filter cushion member comprises a resilient, non-absorbent, open cell member, said support members being embedded in said resilient, non-absorbent open cell member.

5. The absorbent device as claimed in claim 4 wherein said resilient non-absorbent open cell member includes top and bottom portions having a plurality of aligned pairs of transverse reliefs, one support member being disposed in each pair of aligned reliefs between said top and bottom portions.

6. The absorbent device as claimed in claim 5 wherein said support members are radially noncompressive, elongated members extending transversely across said resilient non-absorbent open cell member.

7. The absorbent device as claimed in claim 5 further including an absorbant member disposed between said top and bottom portions of said resilient, non-absorbant open cell member and between said support members.

8. The absorbent device as claimed in claim 4 wherein said filter cushion member is encased in a non-absorbent, moisture permeable covering.

9. An absorbent device for a bed or the like comprising:
   a flexible bag like member having a moisture impervious perimeter and bottom, a non-absorbent moisture permeable top and internal divider subdividing the bag like member into an upper compartment and a lower compartment, said bag like member including means for opening and closing an access into said lower compartment;

a non-absorbent, moisture permeable cushion in said upper compartment; and an absorbent element in the lower compartment, said absorbent element being insertable into and removable from said lower compartment through said access.

10. The absorbent device as claimed in claim 9 wherein said non-absorbent, moisture permeable cushion is tightly encased in a non-absorbent, moisture permeable casing, and a non-absorbent, moisture impervious bag like member is sealedly attached to said casing along a top perimeter edge of said casing forming said lower compartment and said non-absorbent moisture impervious perimeter and bottom of said bag like member.

11. The absorbent device as claimed in claim 10 including a zippered opening in said non-absorbent, moisture impervious bag like member opening into said lower compartment.

12. The absorbent device as claimed in claim 10 wherein said absorbent element is encased in a non-absorptive, moisture permeable covering.

13. The absorbent device as claimed in claim 12 wherein said absorbent element includes support means for preventing compression of said absorbent element under the influence of an external force.

14. The absorbent device as claimed in claim 13 wherein said support means includes a plurality of elongated spaced apart cylindrical members in said absorbent element.

15. The absorbent device as claimed in claim 14 wherein said covering encasing said absorbent element includes a handle.

16. The absorbent device as claimed in claim 14 wherein said absorbent element is disposed between mating halves of a resilient, non-absorbent filter cushion element, said filter cushion element including a plurality of relieved portions with said support members disposed in said relieved portions between said mating halves.

17. The absorbent device as claimed in claim 16 wherein said absorbent element comprises a cotton liner disposed between said mating halves of said filter cushion element and between at least some of said support members.

18. The absorbent device as claimed in claim 17 wherein said non-absorbent, moisture permeable cushion in said upper compartment is about ½ inch thick and said filter cushion element in said lower compartment is about 3 to 4 inches thick.

19. An absorbent device for a bed or the like comprising:

a flexible bag like member having a moisture impervious bottom, moisture impervious perimeter sidewalls and perimeter end walls, a non-absorbent, moisture permeable top and a moisture permeable internal divider subdividing the bag like member into a an upper compartment and a lower compartment, said bag like member including a closable access opening into at least the lower compartment;

a non-absorbent, moisture permeable cushion in said upper compartment; and a filter cushion member in said bottom compartment including a resilient, moisture permeable filter cushion element and a moisture absorbing element internally of said moisture permeable filter cushion element, said filter cushion member further including means for limiting compression of said resilient filter cushion element.

* * * * *